United States Patent
Danielyan et al.

(10) Patent No.: US 9,701,941 B2
(45) Date of Patent: *Jul. 11, 2017

(54) CELL SELECTION METHOD AND CELLS OBTAINED THEREFROM

(71) Applicant: Eberhard Karls Universitaet Tuebingen Medizinische Fakultaet, Tuebingen (DE)

(72) Inventors: Lusine Danielyan, Tuebingen (DE); Christoph Gleiter, Tuebingen (DE); Matthias Schwab, Stuttgart (DE); Richard Schäfer, Niedernhausen (DE)

(73) Assignee: Eberhard Karls Universitaet Tuebingen Medizinische Fakultaet, Tuebingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/634,484

(22) Filed: Feb. 27, 2015

(65) Prior Publication Data

US 2015/0166954 A1    Jun. 18, 2015

Related U.S. Application Data

(63) Continuation of application No. PCT/EP2013/067300, filed on Aug. 20, 2013.

(30) Foreign Application Priority Data

Aug. 27, 2012   (DE) .................. 10 2012 107 879

(51) Int. Cl.
   *C12M 3/00*    (2006.01)
   *C12N 5/079*   (2010.01)
   (Continued)

(52) U.S. Cl.
   CPC ............ *C12N 5/0622* (2013.01); *A61K 35/28* (2013.01); *C12M 23/12* (2013.01); *C12M 33/14* (2013.01);
   (Continued)

(58) Field of Classification Search
   None
   See application file for complete search history.

(56) References Cited

U.S. PATENT DOCUMENTS

2008/0274086 A1* 11/2008 Yu ..................... C12N 5/0623
                                                   424/93.7

FOREIGN PATENT DOCUMENTS

CN         201495228 U      6/2010
KR    10 2010 0117869      11/2010
(Continued)

OTHER PUBLICATIONS

Honczarenko et al, Stem Cells, 2006, vol. 24, pp. 1030-1041.*
(Continued)

*Primary Examiner* — Allison Fox
(74) *Attorney, Agent, or Firm* — Klarquist Sparkman, LLP

(57) ABSTRACT

The present invention relates to a method for the in vitro selection of at least one therapeutic cell subpopulation from an original cell population of eukaryotic cells, as well as to the therapeutic cell subpopulation selected by the method, which can be used for the treatment of diseases of tissues or organs. The selected cells are highly migrative and the method according to the invention provides for the selection of these highly migrative subpopulations from a sample comprising a mixture of cells.

10 Claims, 3 Drawing Sheets

(51) Int. Cl.
| | |
|---|---|
| C12M 1/26 | (2006.01) |
| C12M 1/34 | (2006.01) |
| C12M 1/00 | (2006.01) |
| C12N 5/00 | (2006.01) |
| G01N 33/50 | (2006.01) |
| C12M 1/32 | (2006.01) |
| A61K 35/28 | (2015.01) |
| C12N 5/0775 | (2010.01) |
| B01L 3/00 | (2006.01) |

(52) U.S. Cl.
CPC ............ *C12M 41/46* (2013.01); *C12M 47/04* (2013.01); *C12N 5/0068* (2013.01); *C12N 5/0087* (2013.01); *C12N 5/0662* (2013.01); *G01N 33/5029* (2013.01); *B01L 3/502761* (2013.01); *C12N 2501/05* (2013.01); *C12N 2501/10* (2013.01); *C12N 2501/20* (2013.01); *C12N 2501/30* (2013.01)

(56) References Cited

FOREIGN PATENT DOCUMENTS

| WO | WO 03/078565 A1 | 9/2003 |
|---|---|---|
| WO | WO 2014/033009 A1 | 3/2014 |

OTHER PUBLICATIONS

Machine translation of Dai et al CN 201495228, published Jun. 2, 2010.*

International Search Report and Written Opinion from PCT Patent Application No. PCT/EP2016/054055 13 pages (mailed Apr. 14, 2016).

Nichols et al., "Neurogenic and Neuro-protective Potential of a Novel Subpopulation of Peripheral Blood-derived CD133+ ABCG2+CXCR4+ Mesenchymal Stem Cells: Development of Autologous Cell-based Therapeutics for Traumatic Brain Injury," *Stem Cell Research & Therapy* 4(1): 3 (Jan. 6, 2013).

Zhu et al., "A Protocol for Isolation and Culture of Mesenchymal Stem Cells from Mouse Compact Bone," Nature Protocols 5(3):550-560 (Mar. 1, 2010).

Brinke et al., "Generation of Dendritic Cells for Immunotherapy is Minimally Impaired by Granulocytes in the Monocyte Preparation," *Immunobiology* 211(6-8):633-640 (Sep. 14, 2006).

Chen, "Boyden Chamber Assay," *Methods in Molecular Biology* 294:15-22 (Sep. 28, 2005).

Huang et al., "Evaluation of Cancer Stem Cell Migration Using Compartmentalizing Microfluidic Devices and Live Cell Imaging," *Journal of Visualized Experiments* 58(E3297):1-6 (Dec. 2011).

Kawaguchi et al., "A New Co-Culture Method Utilizing a Dual Compartment Cell-Allocation Apparatus for Observation and Identification of Synapse Formation in vitro," *Brain Research* 594(2):284-289 (Oct. 30, 1992).

Kelly et al., "Transplanted Human Fetal Neural Stem Cells Survive, Migrate, and Differentiate in Ischemic Rat Cerebral Cortex," *PNAS* 101(32):11839-11844 (Aug. 10, 2004).

Lee et al., "Intracerebral Transplantation of Bone Marrow-Derived Mesenchymal Stem Cells Reduces Amyloid-Beta Deposition and Rescues Memory Deficits in Alzheimer's Disease Mice by Modulation of Immune Responses," *Stem Cells* 28:329-343(2010).

Lois et al., "Chain Migration of Neuronal Precursors," *Science* 271:978-981 (Feb. 16, 1996).

Park et al., "Inflammation and Stem Cell Migration to the Injured Brain in Higher Organisms," *Stem Cells and Development* 18(5):693-701 (2009).

Wang et al., "Neural Stem Cells Transplantation in Cortex in a Mouse Model of Alzheimer's disease," *The Journal of Medical Investigation* 53:61-69 (2006).

Wray et al., "Evidence that Cells Expressing Luteinizing Hormone-Releasing Hormone mRNA in the Mouse are Derived from Progenitor Cells in the Olfactory Placode," *PNAS* 86:8132-8136 (Oct. 1989).

Zigmond et al., "Chemotaxis Assays for Eukaryotic Cells," *Current Protocols in Cell Biology* (May 1, 2001).

* cited by examiner

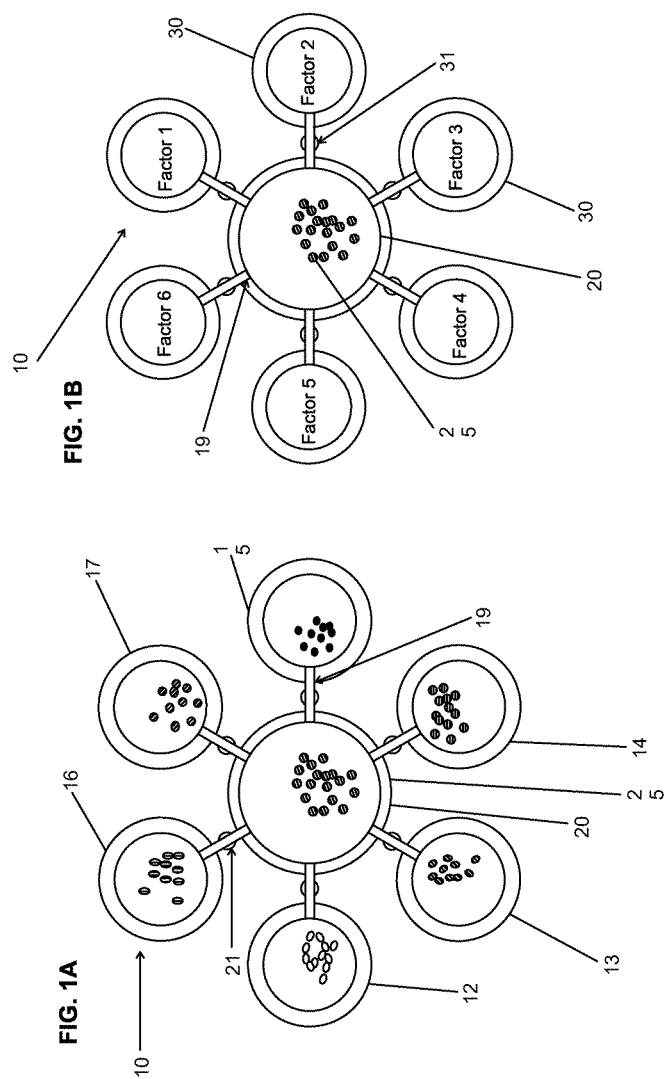

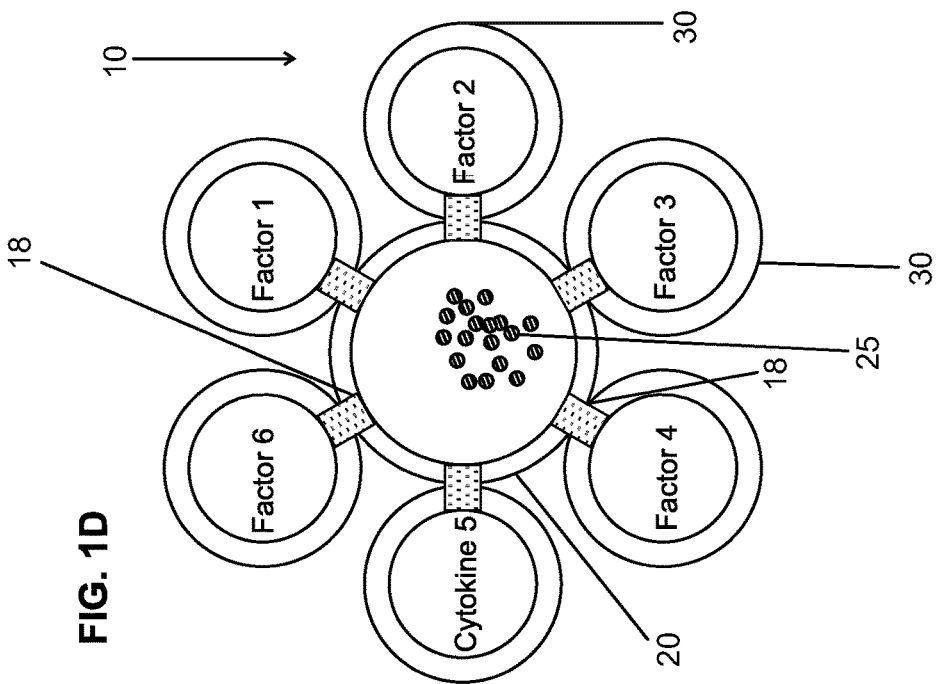
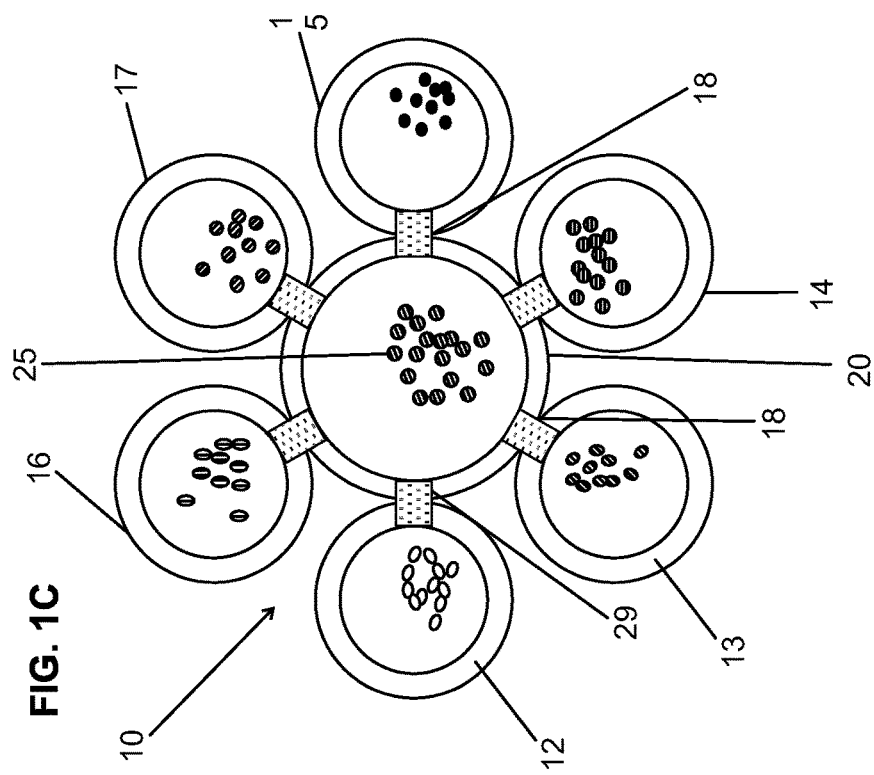

CELL SELECTION METHOD AND CELLS OBTAINED THEREFROM

CROSSREFERENCES TO RELATED APPLICATIONS

This application is a continuation of international patent application PCT/EP2013/067300, filed on Aug. 20, 2013 designating the U.S., which international patent application has been published in German language and claims priority from German patent application DE 102012107879.3, filed on Aug. 27, 2012.

BACKGROUND OF THE INVENTION

The present invention relates to a method for the in vitro selection of at least one cell subpopulation from an original cell population of eukaryotic cells as well as to the cells selected with this method and the use thereof.

In recent years cell-based therapy of degenerative diseases has proven to be an interesting and potent therapeutic method for treating neurodegenerative diseases of the central nervous system (CNS), chronic liver diseases, heart diseases, arthritis or also tumors, among other things. Cell-based therapy is based on the replacement of injured cells, damaged cells, and/or cells which are impaired or degenerated in terms of their ability to regenerate and/or their normal activity with transplanted cells, which are either natural, i.e., non-modified, native cells or genetically modified cells. The replacement of these degenerated cells with native or genetically modified cells can be supported by, for example, trophic factors. As already mentioned, in the cell therapy method new cells are introduced into a diseased or degenerated tissue in order to regenerate the tissue that is diseased because of degenerated or no longer functional cells and thereby treat specific diseases. The cells presently used in the course of cell therapy are in particular stem cells or stem cell precursor cells, which are either autologous, i.e., obtained from the patient who is to be treated, or allogeneic, i.e., cells that were obtained from a donor. As a rule the stem cells or stem cell precursor cells differentiate in the tissue into which they are introduced into the cells that were originally present in the tissue, and do so under the influence of the surrounding tissue itself. Alternatively, at the present time use is also made of mature functional cells or genetically modified cells, which as a rule have been genetically modified to produce a specific substance that is either needed or lacking in the tissue in question.

Especially when stem cells are used, it is desirable to select the stem cells that are particularly active or possess an elevated potential to differentiate into the mature cells of the tissue into which said stem cells are introduced.

The mesenchymal stem cells presently used are multipotent adult stem cells and possess immunomodulatory properties, and are able to proliferate rapidly. They can therefore be used for a wide range of treatments, including for immunomodulatory therapy, for bone and cartilage regeneration, for myocardial regeneration, as well as for neurological or musculoskeletal diseases. To this end, the mesenchymal stem cells can either be introduced prior to their differentiation into the tissue in question, or they can be induced to differentiate in vitro into the desired cells in question and then introduced into the injured or degenerated tissue once they have differentiated. The cells, i.e., either the differentiated cells or the mesenchymal stem cells, then integrate themselves at the degeneration site and either replace the injured or degenerated tissue or counteract a progression of the injury/degeneration through their trophic and immunomodulatory activity, thereby partially or completely restoring the function of the organ or tissue.

As already mentioned above, for the regeneration of degenerated tissue in the course of cell therapy use can also be made of cells that act in an immunomodulatory manner in order to secrete soluble factors such as cytokines, chemokines, or growth factors, which express their efficacy in the vicinity of the introduced cells.

Therapy with adult stem cells represents an important milestone, particularly in the field of treating CNS diseases. In this case the therapeutic goal is to counteract the decline, i.e., the degeneration, of neurons by targeted protection or by new formation.

Accordingly, cell-based therapy has since been employed in nearly all kinds of neurodegenerative diseases (see for example Lee et al., Stem Cells 28: 329-343; Wang et al., 2006, Journal of Medical Investigation 53: 61-69) as well as in numerous acute CNS diseases such as traumatic brain injury, strokes, and also in tumor diseases.

In spite of the therapeutic effects of stem cells that have been demonstrated in preclinical studies, there are numerous problems associated with the cell implant techniques: when implanting stem cells there is often the risk that the transplanted cells will not achieve and maintain the desired phenotype, or that the transplanted cells will not survive in a stable therapeutic concentration in the central nervous system, or that an immune reaction will be triggered in the recipient tissue. Moreover, there is also the risk of the transplanted cells migrating from the transplant site and thus failing to bring about a regeneration of the degenerated tissue.

Against this background, it would be desirable to be able to select a subpopulation from the respective stem cell type and development stage, and to be able to evaluate this subpopulation for the cell-based therapy of degenerative diseases in terms of whether it possesses a better efficacy and safety profile than non-selected populations. Such a selection would be desirable for animal experiments as well as for the treatment of animals and humans, and consequently mammals in general.

Accordingly, the problem addressed by the present invention is that of providing a novel means with which cells that can be used successfully in cell therapy can be selected, or of providing such cells in general.

SUMMARY OF THE INVENTION

According to the invention, this problem is solved by a method for the in vitro selection of at least one therapeutic cell subpopulation from an original cell population of eukaryotic cells, wherein the therapeutic cell subpopulation can be used for the treatment of diseases of tissues or organs, and wherein the method has the following steps: a) Addition of an original cell population to a starting reservoir, which is connected via at least one selection means having at least one opening to at least one selection reservoir, wherein the at least one opening of the at least one selection means has a diameter of 3 µm to 500 µm; b) Addition of at least one cell culture medium to the at least one selection reservoir; c) Culturing of the original cell population for a period of 15 min to 48 hours, within which period a cell subpopulation migrates through the at least one opening of the selection means towards the at least one selection reservoir; d) Selection and obtaining of a cell, which is selected from at least one of the cells that migrated as the first to the one hundred thousandth cell through the at least one opening of the selection means into the at least one selection reservoir, in order to obtain a cell subpopulation with an elevated migration potential or tropism to a certain cell type compared to the original cell population.

Furthermore, the problem addressed by the invention is solved by the cells obtained by the method of the invention with elevated or high migration potential or tropism to a certain cell type, particularly to a cell type of the organ or tissue to be potentially treated, and also by the use thereof in the treatment of diseases and/or the use thereof in the production of a drug for treating diseases.

The problem addressed by the invention is completely resolved in this manner.

With the method of the invention it is possible to select, from original cell populations, subpopulations that possess an elevated migration potential or tropism to (a) specific cell type(s) of the organ to potentially be treated and that are especially potent therapeutically because of this potential.

For example, the targeted selection and isolation of subpopulations of therapeutic cells which have proven to be especially potent in the regeneration of degenerated tissue (such as nerve tissue, for example) is possible with the method of the invention.

By the selection of this subpopulation, it is possible to ensure that the therapeutic cells to be used or introduced in the context of cell therapy migrate faster and in a more targeted manner to the target tissue than would non-selected cells from original populations of the same cell type. A more effective and faster regeneration of the degenerated tissue can thus be effected.

The cell culture medium supplied in step b) can be used with or without adding one of the following: a cytokine/chemokine or growth factor, and/or a cell population from at least one cell type such as neurons, astrocytes, immune-competent cells and tumor cells of the brain, perivascular or vascular or connective tissue cells or parenchymal cells of various organs such as the liver, lungs, spleen, gastrointestinal and urogenital tract organs, skin, muscles, cells isolated from one or more specific tissue(s)/region(s) of an organ, in particular of the brain, such as the hippocampus, olfactory bulb, etc.

Here a "reservoir" is understood to mean any container or any chamber that is suitable for holding and culturing cells. As an example, for the present method use can be made of a container selected from the Petri plates, microtiter or multi-well plates that are standardly used nowadays in the field of cell culture and cell analysis. "Starting reservoir" is understood to mean the reservoir in which the original cell population is applied or introduced, and at least one "selection reservoir" is understood to mean the reservoir/reservoirs into which the cell subpopulation(s) migrates/migrate.

According to the method of the invention, the original cell population is added to the starting reservoir, from which the cell subpopulation(s) migrates/migrate via the at least one opening of the selection means into the at least one selection reservoir within a certain period that depends upon the respective cell subpopulation and the conditions in the starting reservoirs.

In the method of the invention, steps a) and b) can be performed sequentially or simultaneously; the remaining steps are carried out sequentially.

Here "selection means having at least one opening" is understood to mean any element that has at least one, preferably several, opening(s) with the diameter of 3 μm to 500 μm as defined above, with which a selection of the original cell population can be achieved by cells of the original cell population migrating through said at least one opening.

According to the invention, the at least one opening can be selected from at least one channel with a defined diameter of 3 μm to 500 μm, or at least one opening with a diameter of 3 μm to 500 μm. Preference is given to providing a plurality of openings and a plurality of channels, which can have the same diameter or diameters that vary within the specified range.

According to an embodiment, preference is given to the selection means being a membrane with pores. In this embodiment of the selection means, the at least one opening is a pore or a plurality of pores via which the cell subpopulation migrates into the selection reservoirs.

According to another embodiment, preference is given to the selection means having at least one opening being at least one channel with the defined diameter via which the starting reservoir and the at least one selection reservoir are fluid-connected to one another. When provision is made of a plurality of selection reservoirs, the starting reservoir is connected to each of the latter via corresponding channels.

Furthermore, here "therapeutic cell subpopulation" or "therapeutic cell" is understood to mean any subpopulation or any cell, respectively, that can be employed in a targeted and effective manner for the use in cell therapy as explained previously and thus bring about a regeneration of the tissue or organ being treated, e.g., an injured or degenerated tissue or organ. According to the definition, a "therapeutic cell subpopulation" or "therapeutic cell" therefore comprises at least one cell or cell type, for instance adult mesenchymal or neural stem cells, which are applied to or migrate to the degenerated or injured tissue or organ intended to be treated with said therapeutic cell/cell subpopulation. The therapeutic cell/cell subpopulation can originate from any eukaryotic source, from mammals in particular, is preferably a human cell/cell subpopulation, and can occur in various differentiation stages, provided that they are capable of preventing or alleviating the disease to be treated and for which they are intended to be used as cell therapy. Obviously the therapeutic cell/cell subpopulation can either be autologous, i.e., originating from the patient who is to be treated, or allogeneic, i.e., obtained from a donor. As a rule autologous cells are extracted from the patient, manipulated ex vivo, and reintroduced into the patient being treated.

The eukaryotic original cell population and/or the cell subpopulation can be obtained from any organ or tissue, preferably a mammal, including human, organ or tissue, adult or fetal, including bone marrow, nerve tissue, including hippocampus tissue and tissue of the subventricular zone, cerebellum, cortex, basal forebrain, ventral mid-brain, and locus ceruleus. Moreover, use can also be made of populations of mesenchymal or neural stem cells, precursor cells, genetically modified cells, or T-cells.

According to a preferred embodiment of the method of the invention, the original cell population is selected from an original population of embryonic, fetal, or adult stem cells and progenitors from the bone marrow, in particular mesenchymal, hematopoietic stem cells, adipose tissue, umbilical cord blood, nerve tissue, skin, blood, connective tissue, liver, kidneys, lungs, spleen, pancreas; from somatic cells with the potential to transform into induced pluripotent stem cells such as fibroblasts of the skin, brain, liver, or pancreas; from somatic cells with therapeutic potential such as astroglia, hepatic astrocytes, microglia, lymphocytes, macrophages, natural killer cells, T-lymphocytes, mesangial cells of the kidneys, endothelial cells, neurons. According to a preferred embodiment, embryonic cells are included.

Adult mesenchymal stem cells (MSCs) are precursor cells of connective tissue and possess a high differentiation potential; they contribute to the maintenance and regeneration of support and connective tissue such as bones, cartilage, muscles, ligaments, tendons, and adipose tissue and support growth and development of blood precursor cells in bone marrow. MSCs from various tissues (bone marrow, cartilage, adipose tissue, muscle, liver tissue, blood, amniotic fluid) can be cultured and induced to differentiate into various tissues in vitro. Differentiated MSCs are furthermore capable of transforming into another tissue and adapting to new environmental conditions.

Astroglia are the characteristic star-shaped glial cells of the brain and spinal cord. Their functions include the biochemical support of the endothelial cells that form the blood-brain barrier, the supplying of nutrients to nerve tissue, the maintenance of the extracellular ionic balance, and they also play a role in repairing the brain after traumatic injuries.

According to an embodiment of the invention, preference is given to the at least one opening of the selection means having a pore size of 8 to 12 µm.

The selection of this pore size or channels with this diameter in particular enables the isolation of migration-active cells.

According to another embodiment, preference is given to the period in step c) being 15 min to 6 hours.

In in-house experiments, it was possible to select cell types with an elevated migration potential within this period.

Here "migration potential" is understood to mean the property of cells of being able to migrate in certain directions to specific sites. Accordingly, cells with an elevated migration potential move/migrate faster than cells with an average or lower migration potential.

Regardless of the respective migration capacity or respective migration potential (these terms are also used synonymously here), the migration of the cells can also be influenced by specific external signals; this process is also known as chemotaxis.

The migration direction of the cells can be defined by tropism (a target-specific migration to specific cell and tissue types). These cell or tissue types can be in normal physiological condition as well as in pathological condition. The pathological conditions may be characterized as generally disease-relevant, such as inflammation, cell death (including apoptosis or necrosis), hypoxia, ischemia, degeneration, neoplasm, edema, mechanical damage, and may also be characterized by specific markers of the respective disease, such as amyloid beta in Alzheimer's disease and collagen I, III, IV, and VI in liver diseases.

According to the invention, the first cells to move through the at least one opening of the selection means within a specific period into the cell culture medium of the reservoir are the ones that are selected, wherein preference is given to selecting at least one of the cells from among the first to the one hundred thousandth cell, preferably the hundredth cell, to migrate through the at least one opening of the selection means. Accordingly, it is not a specific period of time that is relevant, but the sequence in which the cells move through the at least one opening of the selection means: the cells that are part of the group comprising the first one hundred or first one hundred thousand cells are migrated through the opening of the selection means (i.e., the channels or pores of the membrane) are thus of particular interest for selection.

Particular preference is given to cells out of the first fifty cells to migrate through the at least one opening of the selection means.

In a preferred embodiment, for selection provision is made in particular of those cells that migrate through the at least one opening of the selection means within the period of the first thirty minutes.

The material of the selection means to be used here, i.e., that of the membrane or of the channel, is a material that can be used in the field of cell biology or in vitro biotechnology, and which is inert with respect to the cells, meaning that the cell is unaffected by the properties or the chemical composition thereof, but that said material merely has at least one opening, in particular pores/channels of a certain size or of varying sizes through which cells can migrate.

Examples of membranes that can be used as selection means in the present method of the invention are those sold by the German company Greiner Bio-one, and they are essentially composed of materials such as polyethylene terephthalate or polycarbonate. The channels employed as alternatives to membranes can be composed of glass, quartz glass, plastics (e.g., polystyrene) or similar materials or can comprise these materials, the structure of which permits the visual observation of living cells through microscopes. According to the invention, the membrane serves as a type of separation layer between at least the first and the second reservoir.

When use is made of at least one channel as a selection means between the first and the second reservoir, said at least one channel serves as a connection between the two reservoirs.

According to the invention, in preferred embodiments provision can also be made of two, three, four, five, or six or more selection reservoirs, which are each separated from the first starting reservoir (into which the original cell population is introduced) by a selection means having at least one opening.

According to another preferred embodiment of the method of the invention, use is made of at least 2, 3, 4, 5, or 6 reservoirs arranged sequentially downstream for selection. In this structure, in which two or more reservoirs are placed separately in a container (e.g., Petri plate) and are connected by one or more channels, for example, the cell selection is effected by migration from the starting reservoir into the others via an intermediate reservoir, from which the cell is selected before it reaches the target reservoir.

By providing a plurality of selection reservoirs that are optionally equipped with certain substances or other cells, the above-mentioned embodiments have the advantage that cell subpopulations can be directed specifically by the contents of the selection reservoirs to migrate into these reservoirs, and cell subpopulations (and cells therefrom) capable of asserting themselves under disease-simulating conditions in different selection reservoirs can be selected. To this end, the phenomenon of tropism to specific cell types and/or disease conditions is chosen for selection of the cell populations.

The tropism of some stem cells to certain areas of the brain (as has been described for certain neurons, see for example Wray et al., 1989 and Lois et al., 1996) or the lesion/inflammation- or degeneration-oriented migration of stem cells in many neurodegenerative models and tumor models (Kelly et al., 2004, Park et al., 2009) is also exploited in the scope of the present invention.

Hence according to a preferred embodiment of the method of the invention, the cell culture medium present in the at least one reservoir, particularly in the at least one selection reservoir, is selected from tissue type- or cell type-specific culture media with or without specific additives (for example SDF-1 a/CXCL 12, Cdc42, integrins, Wnt signal cascade activators, components of the extracellular matrix) that can influence the growth or differentiation, activation, and migration/chemotaxis of the cells. In particular, such additives include hormones, cytokines, growth factors (nerve growth factor [NGF], basic fibroblast growth factor [bFGF], epidermal growth factor [EGF], brain-derived neurotrophic factor [BDNF], insulin-like growth factor [IFG-1], platelet derived growth factor [PDGF], transforming growth factor-b [TGF-b], and other molecules that can influence cells in their activation state, for instance inflammation mediators, e.g., interleukins such as IL-1, 2, 6 or peptides with inflammatory/toxic or anti-inflammatory or anti-apoptotic activity such as IL-10, 4, 5, erythropoietin, etc.

For example, the cell culture medium DMEM (Dulbecco's Modified Eagle's Medium) can be used, which is available on the market from several different suppliers. In the field of cell culture, DMEM is a standardly employed medium, which generally also contains glucose and vitamins in addition to amino acids and salts.

According to an alternative of the aforementioned embodiment of the method of the invention, the cell culture medium can also be, for example, DMEM without glucose or with LPS (lipopolysaccharides).

According to another embodiment of the method of the invention, preference is given to the culture medium present in the at least one selection reservoir also having cell types that are selected from native or genetically modified cell types.

Hence in this embodiment are already present in the culture medium in the at least one selection reservoir into which the cell subpopulations migrate prior to the migration of said cell populations into said at least one selection reservoir. These cell types can be selected in such a way that, by virtue of their presence in the at least one selection reservoir, conditions that are specific for certain degenerative diseases will be simulated.

According to another embodiment, preference is given to selection of the cells from at least one of the following: cells with which models for neurodegenerative diseases can be simulated in vitro, cells with which models for tumors can be simulated in vitro, cells with which models for inflammatory diseases can be simulated in vitro, cells with which models for traumatic or oxidative stress conditions can be simulated in vitro.

For instance, it is thus possible to simulate the conditions of Alzheimer's disease with APP (amyloid precursor protein)-overexpressing cells, the conditions of Parkinson's disease with alpha synuclein-expressing cells, or tumor or trauma conditions in general that are characterized by oxygen deficiency (hypoxia), oxidative stress, and/or inflammations. Various cell models for diseases of mammals, in particular humans, are known in the cell culture research field and can be used accordingly in the present method.

By virtue of the presence of cells in the at least one selection reservoir, the cell subpopulations from the original cell population, which migrate from the starting reservoir via the at least one selection means having at least one opening into the at least one selection reservoir, can be influenced in their differentiation/activation by the conditions defined by the cell types.

Hence in a preferred embodiment of the method of the invention for the selection of a cell subpopulation specialized for a very specific organ or tissue region, the cell mixture or original cell population is added to the starting reservoir in such a way that, owing to the presence of several different cell types and/or substances in respective different selection reservoirs that are separated from the starting reservoir by selection means having openings, the original cell population has the choice of several "final targets". Because subpopulations form with the method of the invention and then migrate to different selection reservoirs and have different specificities as a result, the selection of the cell subpopulations is thus very specific.

Furthermore, according to another embodiment preference is given to adding at least one other substance to the cell culture medium for inducing the migration of cells through the at least one opening of the selection means, which substance is selected from the group comprising chemoattractants, pharmacologically active substances, hormones, or growth factors.

The use of these substances will be selected on the basis of each desired cell subpopulation type, and with respect to the organ or tissue to be regenerated. Examples of such uses include amyloid beta for CNS tissue in Alzheimer's disease, HIF1, inflammation mediators (interleukins) for tumors and ischemic lesions of the CNS and other organs.

By using these substances, organ-specific and tissue-specific mammalian cell types can thus be selected as cell populations with high migration potential.

Furthermore, especially vigorous cell subpopulations (e.g., MSCs) can be selected by creating degenerative conditions in the at least one selection reservoir (whether by means of a cell model or by means of a suitable composition of the cell culture medium, optionally without additives).

In this context with a plurality of selection reservoirs, obviously different conditions and/or cell types can be present therein. In this manner the cell subpopulations can be selected with respect to the different conditions or cell types, depending upon which of the different selection reservoirs the cell subpopulation migrates into.

Accordingly, the present invention also relates to the cell subpopulation, i.e., cells with elevated migration potential, obtained by the methods of the invention, particularly for treating diseases of mammals or for producing a drug for treating diseases of mammals, particularly humans.

The cells or original cell populations are thus preferably of human origin, but can be selected with respect to any mammal and used for the mammal from which the original cell population was obtained. Preferably, the cells are eukaryotic cells, and the highly migrative subpopulation is a eukaryotic cell subpopulation, preferably a highly migrative MSC subpopulation.

Particular preference is given to using the cells with elevated migration potential obtained by the method of the invention for treating diseases selected from the group comprising tumors, traumas, lesions, degenerative diseases of the brain, liver, kidneys, lungs, heart, gastrointestinal tract, muscles, skin, blood, and bones.

Because the cells or cell subpopulations selected by the method of the invention are characterized by a high migration capacity or high migration potential, they are especially well suited for use in cell therapies in which the cells to be used in the scope of the cell therapy cannot be used directly in the organ or tissue region being treated, for example because of anatomical reasons. This is particularly advantageous with diseases in which it is important that the cells also reach peripheral regions or the CNS, in order to replace the degenerated tissue therein. In an advantageous manner, it is thus possible for the therapeutically employed cells not to be introduced or applied to sites in the tissue that are in proximity or adjacent to the diseased or degenerated cells (e.g., intravenous, intra-arterial, intrathecal application in CNS diseases).

Accordingly, the cells with high migration potential selected by the method of the invention can be used specifically for treating the above-mentioned diseases.

Accordingly, preference is given here to selecting the adult cell with high migration potential from at least one of the following: mesenchymal stem cells, hematopoietic stem cells, neural precursor cells, somatic cells with the potential to transform into induced pluripotent stem cells, for example fibroblasts of the skin, brain, liver, pancreas, astroglia, hepatic astrocytes, microglia, lymphocytes, macrophages, natural killer cells, T-lymphocytes, mesangial cells of the kidneys, endothelial cells, neurons. According to a preferred embodiment, also embryonic cells are included.

Accordingly, the present invention also relates to a pharmaceutical composition having at least one of the above-described cells selected according to the invention in combination with at least one pharmaceutically acceptable carrier.

For this purpose pharmaceutically acceptable carrier is understood to mean any excipient, additive, or pharmaceutical carrier that is typically used in the field of medicinal cell therapy, and which simplifies or enables the administration of the selected cells.

The therapeutically effective dose of the cells with high migration potential selected by the method of the invention to be used in the scope of the invention is thus the dose that brings about the regeneration of the degenerated or damaged tissue. The precise effective dose for a given patient thus depends in particular upon the latter's size and weight and state of health, as well as on the nature and extent of the disease.

The pharmaceutical composition can be administered to a patient in a variety of different forms, which are adapted to the chosen route of administration, specifically parenteral, oral, intraperitoneal, transdermal, etc.

The cells for the cell therapy are typically transplanted. For this purpose, particular preference is given to non-invasive applications, for example, an intranasal application for CNS diseases.

As mentioned above, the pharmaceutical composition can also have pharmaceutically acceptable carriers, binding agents, diluting agents, excipients or adjuvants. The selection of a pharmaceutical carrier, excipient, or other additive can be made on the basis of the intended administration route and standard pharmaceutical practice. As pharmaceutically acceptable carrier use can be made of solvents, extenders, or other liquid binding media such as dispersing or suspending agents, surfactants, isotonic agents, spreaders or emulsifiers, preservatives, encapsulating agents, solid binding media or lubricants, depending upon what is best suited for the respective dose regime and is likewise compatible with the combination of the invention. An overview of such additional ingredients can be found in, for example, A. Kibbe: Handbook of Pharmaceutical Excipients, 3rd edition, 2000, American Pharmaceutical Association and Pharmaceutical Press.

The present invention further relates to the use of a cell culture reservoir system having a starting reservoir, at least one selection means having at least one opening, as well as at least one selection reservoir, wherein the opening has a diameter of 3 to 500 µm, in the selection of at least one cell subpopulation with elevated migration potential or a tropism to a specific cell type.

As mentioned above, as a consequence of the present invention the suitability of such a system for the targeted selection of cells was tested and the system was successfully used for the first time.

Other advantages emerge from the following description and from the appended figures.

Obviously the aforementioned features as well as the ones that will be explained in the following are not only usable in each of the combinations listed, but also in other combinations or individually without exceeding the scope of the present invention.

BRIEF DESCRIPTION OF THE DRAWINGS

Exemplary embodiments of the invention are illustrated in the figures and will be explained in more detail in the following description. Shown are:

FIG. 1A-1D An embodiment of the use of the reservoir system according to the invention with an illustrative arrangement of cell culture reservoirs with channels (A and B) or membranes (C and D) as openings or selection means, respectively, for carrying out the method of the invention; with selection of the subpopulation with respect to certain brain regions (A and C) or with respect to toxic, disease-relevant conditions (B and D)

DESCRIPTION OF PREFERRED EMBODIMENTS

Figure 2:
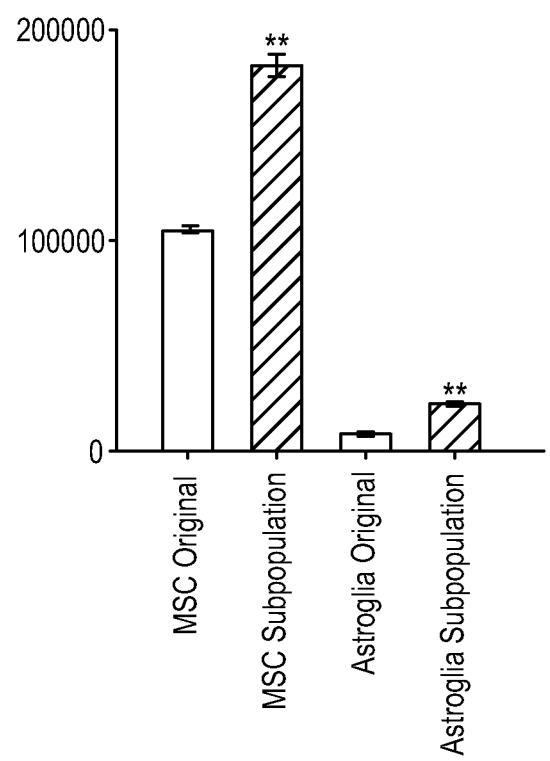
FIG. 2 A diagram showing the migration capacity of non-selected original MSCs or original astroglia compared to a selected subpopulation.

Shown in FIG. 1A is a schematic reservoir system 10 with six selection reservoirs 12, 13, 14, 15, 16, 17, which are arranged in a circle around a central starting reservoir 20. Different cell types, which in the example shown in FIGS. 1A and 1C are different brain cell types, are added to the selection reservoirs. As a selection means, in FIGS. 1C and 1D provision is made of a membrane 18, which has pores 29 for openings that are represented by a dotted fill pattern in FIGS. 1C and D. In FIGS. 1A and 1B, provision is made of channels 19 as selection means, via which the starting reservoir 20 is connected to selection reservoirs 30. The system 10 in FIGS. 1A and 1B furthermore has intermediate reservoirs 21.

Via the pores 29 of the membrane 18 or channels 19, cells migrate from a cell mixture 25 out of the starting reservoir 20 towards individual selection reservoirs 12, 13, 14, 15, 16, 17 so that after a certain point in time, there will be different subpopulations of, e.g., mesenchymal stem cells in different intermediate reservoirs 21, which subpopulations will have a respective specificity for the brain cell types in question. The cells thus selected from the intermediate reservoirs 21 can then be used specifically for diseases of the part of the brain for which they exhibited specificity.

A similar construction for a reservoir system is shown in FIGS. 1B and D, wherein in the embodiment shown in FIGS. 1B and D, different cytokines are added to the different selection reservoirs 30. After their selection in the different selection reservoirs 30 (in D) or in the intermediate reservoirs 31 (in B), the cells 22 migrating through the pores of the membrane 18 in D or through the channels in B to the individual and different selection reservoirs 30 can then be selected for therapy on the basis of the medium with which a specific disease was simulated.

The results from analyses of the migration capacity of various cell types are shown in FIG. 2. In these analyses a distinction was made between an original population of MSCs (oMSC) and a selected MSC subpopulation (sMSC), as well as between original astroglia and a selected astroglia subpopulation.

The comparison of the migration speed over a 4 hour period shows that in each case the selected subpopulations of MSCs (sMSC) and astroglia (sAstroglia) migrated faster to the primary culture than did the respective original populations.

The comparison of the migration speed over a 4 hour period shows that in each case the selected subpopulations of MSCs (sMSC) and astroglia (sAstroglia) migrated faster to the primary culture than did the respective original populations.

What is claimed is:

1. A method for the in vitro selection of at least one therapeutic mesenchymal stem cell, wherein the therapeutic mesenchymal stem cell is from a mesenchymal stem cell subpopulation selected from an original mesenchymal stem cell population, wherein the therapeutic mesenchymal stem cell can be used for the treatment of diseases of tissues or organs, and wherein the method has the following consecutive steps:
   a) adding an original mesenchymal stem cell population to a first starting reservoir, which is connected via at least one selection means having at least one opening to at least two selection reservoirs, wherein the at least one opening of the at least one selection means has a diameter of 8 µm to 12 µm;
   b) adding at least one cell culture medium to the at least two selection reservoirs;
   c) culturing the original mesenchymal stem cell population for a period of 15 min to 6 hours, within which period a mesenchymal cell subpopulation migrates through the at least one opening of the selection means towards at least one of the at least two selection reservoirs; and
   d) selecting and obtaining at least one of the mesenchymal stem cells that migrated as the first to the one hundred thousandth cell through the at least one opening of the selection means into at least one of the at least two selection reservoirs, in order to obtain a mesenchymal stem cell with an elevated migration potential or tropism compared to the original mesenchymal stem cell population,
thereby selecting the at least one therapeutic mesenchymal stem cell.

2. The method of claim 1, wherein the original mesenchymal stem cell population is a population of adult mesenchymal stem cells from the bone marrow, adipose tissue, umbilical cord blood, nerve tissue, skin, blood, connective tissue, liver, kidneys, lungs, spleen, and/or pancreas.

3. The method of claim 1, wherein provision is made of at least 3, 4, 5, or 6 selection reservoirs.

4. The method of claim 1, wherein the cell culture medium in step b) also comprises: a cytokine, a chemoattractant, an inflammation mediator, a pharmacologically active substance, a hormone, a growth factors, a cell population of native cell types, and/or a cell population of genetically modified cell types.

5. The method of claim 4, wherein the cell population of genetically modified cell types is selected from the group consisting of neurons, astrocytes, immune-competent cells, tumor cells of the brain, perivascular cells, vascular cells, connective tissue cells, and parenchymal cells.

6. The method of claim 4, wherein the cell population of genetically modified cell types are selected from the group consisting of a) cells with which models for neurodegenerative diseases can be simulated in vitro, b) cells with which models for tumors can be simulated in vitro, c) cells with which models for inflammatory diseases can be simulated in vitro, and d) cells with which models for traumatic, hypoxic, ischemic or oxidative stress conditions can be simulated in vitro.

7. The method of claim 5, wherein the parenchymal cells are from a liver, a lung, a spleen, a gastrointestinal tract, a urogenital tract, skin, or a muscle.

8. The method of claim 5, wherein the parenchymal cells are isolated from one or several specific region(s) of an organ, wherein the organ is the brain.

9. The method of claim 1, wherein the original mesenchymal stem cell population is bone marrow mesenchymal stem cells.

10. The method of claim 9, wherein the cell culture medium in step b) further comprises a genetically modified cell.

* * * * *